United States Patent [19]
Mateo de Acosta del Rio et al.

[11] Patent Number: 5,891,996
[45] Date of Patent: Apr. 6, 1999

[54] HUMANIZED AND CHIMERIC MONOCLONAL ANTIBODIES THAT RECOGNIZE EPIDERMAL GROWTH FACTOR RECEPTOR (EGF-R); DIAGNOSTIC AND THERAPEUTIC USE

[75] Inventors: Cristina Maria Mateo de Acosta del Rio; Rolando Pérez Rodríguez; Ernesto Moreno Frías, all of Havana, Cuba

[73] Assignee: Centro de Inmunologia Molecular, Havana, Cuba

[21] Appl. No.: 560,558

[22] Filed: Nov. 17, 1995

[30] Foreign Application Priority Data

Sep. 17, 1972 [WO] WIPO ............................. WO9215683
Nov. 18, 1994 [CU] Cuba .......................................... 128/94

[51] Int. Cl.$^6$ ......................... C07K 16/28; A61K 39/395
[52] U.S. Cl. ................................ 530/387.3; 530/388.22; 424/133.1; 424/143.1
[58] Field of Search .............................. 424/133.1, 141.1, 424/139.1, 143.1; 530/387.3, 387.9, 388.22, 388.85, 389.1; 435/328, 333

[56] References Cited

U.S. PATENT DOCUMENTS

| | | |
|---|---|---|
| 4,943,533 | 7/1990 | Mendelsohn . |
| 5,470,571 | 11/1995 | Herlyn . |
| 5,530,101 | 6/1996 | Queen . |

FOREIGN PATENT DOCUMENTS 0 586 002 A2    3/1994    European Pat. Off. .

OTHER PUBLICATIONS

Article entitled: Cloning immunoglobulin variable domains for expression by the polymerase chain reaction. Authors: Rosaria Orlandi, Detlef H. Gussow, Peter T. Jones and Greg Winter. Published in the Proc. Natl. Acad. Sci. USA vol. 86, pp. 3833–3837, May 1989.

Catherine A. Kettleborough et al., "Isolation of tumor cell-–specific single–chain Fv from immunized mice using phage–antibody libraries and the re–construction of whole antibodies from these antibody fragments", Eur. J. Immunol., vol. 24, 1994, pp. 952–955.

Mayumi Naramura et al., "Therapeutic potential of chimeric and murine anti–(epidermal growth factor receptor) antibodies in a metastasis model for human melanoma", Cancer Immunology Immunotherapy, vol 37, 1993, pp. 343–349.

Catherine A. Kettleborough et al., "Humanization of a mouse monoclonal antibody by CDR–grafting: the importance of framework residues on loop conformation", Protein Engineering, vol. 4, No. 7, 1991, pp. 773–783.

A. Fernandez et al., "A New Monoclonal Antibody for Detection of EGF–Receptors in Western Blots and Paraffin–Embedded Tissue Sections", Journal of Biochemistry, vol. 49, 1992, pp. 157–165.

Paul Carter et al., "Humanization of an anti–p185$^{HER2}$ antibody for human cancer therapy", Proc. Natl. Acad. Sci. USA, vol. 89, May 1992, pp. 4285–4289.

*Primary Examiner*—Toni R. Scheiner
*Assistant Examiner*—Nancy A. Johnson
*Attorney, Agent, or Firm*—Trask, Britt & Rossa

[57] ABSTRACT

New humanized and chimeric monoclonal antibodies that recognize EGF-R and comprise an artificial sequence at least of the FRs of the heavy chain variable region of a human immunoglobulin. The hypervariable regions of both monoclonal antibodies is the following amino acid sequence: light chain:

CDR-1: arg-ser-ser-gln-asn-ile-val-his-ser-asn-gly-asn-thr-tyr-leu-asp;

CDR-2: lys-val-ser-asn-arg-phe-ser;

CDR-3: phe-gln-tyr-ser-hys-val-pro-trp-thr.

Heavy chain:

CDR-1: asn-tyr-tyr-ile-tyr;

CDR-2: gly-ile-asn-pro-thr-ser-gly-gly-ser-asn-phe-asn-glu-lys-phe-lys-thr;

CDR-3: gln-gly-leu-trp-phe-asp-ser-asp-gly-arg-gly-phe-asp-phe.

Use of the antibodies for therapeutical and diagnostic purposes.

8 Claims, 7 Drawing Sheets
1 of 10 Drawings Filed in Color

| | | |
|---|---|---|
| murine VkR3 | D V L M T Q I P L S L P V S L G D Q A S I S C | |
| human. VkR3 | D I Q M T Q S P S S L S A S V G D R V T I T C | |
| murine VkR3 | R S S Q N I V H S N G N T Y L D W Y L Q K P G | |
| human. VkR3 | R S S Q N I V H S N G N T Y L D W Y Q Q T P G | |
| murine VkR3 | Q S P N L L I Y K V S N R F S G V P D R F R G | |
| human. VkR3 | K A P K L L I Y K V S N R F S G V P S R F S G | |
| murine VkR3 | S G S G T D F T L K I S R V E A E D L G V Y Y | |
| human. VkR3 | S G S G T D F T F T I S S L Q P E D I A T Y Y | |
| murine VkR3 | C F Q Y S H V P W T F G G G T K L E I K R A | |
| human. VkR3 | C F Q Y S H V P W T F G Q G T K L Q I T R E | |

FIGURE 2b

| | | |
|---|---|---|
| murine VHR3 | Q V Q L Q Q P G A E L V K P G A S V K L S C K A | |
| human. VHaR3 | Q V Q L Q Q S G A E V K K P G S S V K V S C K A | |
| murine VHR3 | S G Y T F T N Y Y I Y W V K Q R P G Q G L E W I | |
| human. VHaR3 | S G Y T F T N Y Y I Y W V R Q A P G Q G L E W I | |
| murine VHR3 | G G I N P T S G G S N F N E K F K T K A T L T V | |
| human. VHaR3 | G G I N P T S G G S N F N E K F K T R V T I T V | |
| murine VHR3 | D E S S T T A Y M Q L S S L T S E D S A V Y Y C | |
| human. VHaR3 | D E S T N T A Y M E L S S L R S E D T A F Y F C | |
| murine VHR3 | T R Q G L W F D S D G R G F D F W G Q G T T L T | |
| human. VHaR3 | A R Q G L W F D S D G R G F D F W G Q G S T V T | |
| murine VHR3 | V S S | |
| human. VHaR3 | V S S | |

FIGURE 5

```
Hum.VH1R3    Q V Q L Q Q S G A E V K K P G S S V K V S C K A
Res.VH2R3    - - - - - - - - - - - - - - - - - - - - - - - -
Res.VH3R3    - - - - - - - - - - - - - - - - - - - - - - - -
Res.VH4R3    - - - - - - - - - - - - - - - - - - - - - - - -
Res.VH5R3    - - - - - - - - - - - - - - - - - - - - - - - -
Res.VH6R3    - - - - - - - - - - - - - - - - - - - - - - - -
Res.VH7R3    - - - - - - - - - - - - - - - - - - - - - - - -

Res.VH1R3    S G Y T F T N Y Y I Y W V R Q A P G Q G L E W I
Res.VH2R3    - - - - - - - - - - - - - - - - - - - - - - - -
Res.VH3R3    - - - - - - - - - - - - - - - - - - - - - - - -
Res.VH4R3    - - - - - - - - - - - - - - - - - - - - - - - -
Res.VH5R3    - - - - - - - - - - - - - - - - - - - - - - - -
Res.VH6R3    - - - - - - - - - - - - - - - - - - - - - - - -
Res.VH7R3    - - - - - - - - - - - - - - - - - - - - - - - -

Res.VH1R3    G G I N P T S G G S N F N E K F K T R V T I T V
Res.VH2R3    - - - - - - - - - - - - - - - - - K A - - - -
Res.VH3R3    - - - - - - - - - - - - - - - - - - - - - - -
Res.VH4R3    - - - - - - - - - - - - - - - - - - - - - - -
Res.VH5R3    - - - - - - - - - - - - - - - - - K A - - - -
Res.VH6R3    - - - - - - - - - - - - - - - - - - - - - - -
Res.VH7R3    - - - - - - - - - - - - - - - - - K A - - - -

Res.VH1R3    D E S T N T A Y M E L S S L R S E D T A F Y F C
Res.VH2R3    - - - - - - - - - - - - - - - - - - - - - - - -
Res.VH3R3    - - - S T - - - - - - - - - - - - - - - - - - -
Res.VH4R3    - - - - - - - - - - - - - - - - - - - - - - - -
Res.VH5R3    - - - - - - - - - - - - - - - - - - - - - - - -
Res.VH6R3    - - - S T - - - - - - - - - - - - - - - - - - -
Res.VH7R3    - - - S T - - - - - - - - - - - - - - - - - - -

Res.VH1R3    A R Q G L W F D S D G R G F D F W G Q G S T V T
Res.VH2R3    - - - - - - - - - - - - - - - - - - - - - - - -
Res.VH3R3    - - - - - - - - - - - - - - - - - - - - - - - -
Res.VH4R3    T - - - - - - - - - - - - - - - - - - - - - - -
Res.VH5R3    T - - - - - - - - - - - - - - - - - - - - - - -
Res.VH6R3    T - - - - - - - - - - - - - - - - - - - - - - -
Res.VH7R3    T - - - - - - - - - - - - - - - - - - - - - - -

Res.VH1R3    V S S
Res.VH2R3    - - -
Res.VH3R3    - - -
Res.VH4R3    - - -
Res.VH5R3    - - -
Res.VH6R3    - - -
Res.VH7R3    - - -
```

HUMANIZED AND CHIMERIC MONOCLONAL ANTIBODIES THAT RECOGNIZE EPIDERMAL GROWTH FACTOR RECEPTOR (EGF-R); DIAGNOSTIC AND THERAPEUTIC USE

FIELD OF THE INVENTION

This invention is related to the field of immunology and in particular to two new products, which are chimeric and humanized monoclonal antibodies against epidermal growth factor receptor ("EGF-R"), less immunogenic than the original murine monoclonal antibody and with improved effector functions.

This invention also relates to therapeutic and diagnostic compositions comprising these antibodies.

BACKGROUND OF THE INVENTION

The Epidermal Growth Factor (EGF), which is a 53 amino acid polypeptide with a molecular weight of 6045 D, was isolated and purified for the first time from murine submaxillary gland (Cohen S; J Biol Chem (1962) 237, 1555). Later, a similar molecule was obtained from human urine (Cohen S and Carpenter G; (1975) PNAS USA 72, 1317). The action of this polypeptide is mainly performed via its membrane receptor, a 170 KD molecular weight glycoprotein. Its intracellular domain is associated with a tyrosine kinase activity with structural homology to the oncogene v-erb-B showing relation to the malignant transformation process (Heldin C H et al; (1984) Cell 37, 9–20).

High levels of EGF-R have been detected in malignant tumors originating in the epithelium such as breast, bladder, ovarian, vulva, colonic, lung, brain and esophagus cancers. The role played by EGF and its receptor in regulating tumor growth is unknown, but it has been suggested that the EGF-R expression in tumor cells provides a mechanism for autocrine growth stimulation which leads to uncontrolled proliferation (Schlessinger J, Schreiber A B, Levi A, Liberman T and Yarden Y; (1983) Crit Rev Biochem 14(2), 93–111).

It has been reported that EGF produces overgrowth of breast cancer cell lines (Osborne C K et al; (1980) Cancer Research 40, 2361), besides that it modulates the differentiation under some cellular systems (Tonelli C J; Nature (1980) 285, 250–252). These effects on cellular differentiation and proliferation are related to the high expression of EGF-R (Buss J E et al; (1982) PNAS 79, 2574).

The presence of EGF-R in tumor cells has proven to be an indication of a poor prognosis in human breast cancer. Approximately 40% of the breast tumors show specific binding sites of high affinity for the EGF (Perez R, Pascual M R, Macias A, Lage A; (1984) Breast Cancer Research and Treat 4, 189–193). There is also an inverse correlation with the presence of estrogen receptor, indicating EGF-R as an indifferentiation marker or an indicator of the potential capacity of proliferation of the malignant cells.

Other groups have reported that the expression of EGF-R is higher in regional ganglionar metastasis than in primary carcinomas of breast (Sainsbury J R et al; (1985) Lancet 1, 8425, 364–366) and that the expression of the receptor is different in the different histologic subtypes of human breast carcinoma cells, their presence constituting a signal of bad prognosis (Macias A et al; Anti Cancer Research 6: 849–852).

The evidences obtained in different studies have prompted to consider the EGF/EGF-R system as a possible target for therapeutic actions.

We obtained a murine monoclonal antibody (R3), raised against the human placenta as described in European Patent application No. 93202428.4, and found to bind to the external domain of the human EGF-R. It was found to inhibit the binding of EGF at both low and high affinity EGF-R sites.

Passive immunotherapy using monoclonal antibodies against the EGF-R have been the object of multiple investigations, which have demonstrated that the specific recognition of the receptor by the antibody inhibits the EGF binding, with an inhibitory effect on the mitogenic stimulation of malignant cells (Sato J D et al; (1987) Methods in Enzimology 148, 63– 81); but there is evidence that the murine origin of these antibodies produces a human anti-mouse antibody response.

The development of the hybridoma antibody technique by Kohler and Milstein revolutionized the discipline of immunochemistry and provided a new family of reagents with potential applications in clinical diagnosis and immunotherapy (Kohler G, Milstein C; (1975) Nature 256, 495–497). While it has become routine to produce mouse monoclonal antibodies (mAbs) for use in basic research and clinical diagnosis, it has been difficult to use these for in vivo immunotherapy because they have reduced half-life in humans, poor recognition of mouse antibodies effector domains by the human immune system and the foreign immunoglobulin can elicit an antiglobulin response (HAMA response) that may interfere with therapy.

The ability to genetically manipulate antibody genes and then to express these altered genes by transfection techniques enables us to produce mAbs having more desirable properties than the existing hybridoma antibodies. Thus genetic engineering can be used to enhance desired effector functions in antibody molecules and to decrease or eliminate undesired effector functions.

The use of recombinant DNA technology to clone antibody genes has provided an alternative whereby a murine mAb can be converted to a predominantly human form with the same antigen binding properties. S L Morrison in 1984 created mouse-human antibody molecules of defined antigen-binding specificity by taking the variable regions genes of mouse antibody producing myeloma cell lines and joining them to human immunoglobulin constant region (Morrison S L et al; (1984) PNAS USA 81, 6851–6855).

Other authors have attempted to build rodent antigen binding sites directly into human antibodies by transplanting only the antigen binding site, rather than the entire variable domain, from a murine antibody (Jones P T et al; (1986) Nature 321, 522–524; Verhoeven M et al; (1988) Science 239, 1534–1536). Some applications of this method have been developed (Rietchmann L et al; (1988) Nature 332, 323–327; Quee C et al; (1989) PNAS USA 86, 10029–10033), other authors have worked with reshaped antibodies, which included some murine residues in human FRs in order to recover the affinity for the original antigen (Tempest PR; (1991) Biotechnology 9, 266–272).

Orlandi R et al (Proc Natl Acad Sci USA 86, 3833–3837, 1989) disclose the constant regions of the human gamma-1 heavy chain and the human kappa light chain, and suitable cloning vectors therefor.

SUMMARY OF THE INVENTION

The invention provides a chimeric and a humanized mAb which are, in particular, directed to the EGF-R, comprising an antigen-binding site of non-human sources and the constant regions of human origins (chimeric) and the FRs of the variable regions and constant regions of human origins, which are, if necessary, modified in a way that the specificity of the binding can be conserved or restored.

The invention can be used to characterize the hypervariable regions of the antigen-binding site of an antibody against the EGF-R and providing these CDRs within a humanized and chimeric mAb defined as above.

These antibodies can play a role as a therapeutic or diagnostic agent in order to combat tumors with high expression of EGF-R.

This invention provides chimeric and humanized antibodies specific for the EGF-R.

More specifically, the invention provides a chimeric monoclonal antibody comprising variable regions of non-human origin and constant regions of light and heavy chains of human origin, wherein said chimeric monoclonal antibody binds to human EGF-R and inhibits binding of EGF to EGF-R. According to a preferred embodiment of the chimeric monoclonal antibody, the variable regions of the antigen binding sites comprise the amino acid sequences shown in FIG. 1.

Further, the invention provides a humanized monoclonal antibody comprising antigen binding sites (CDRs) of non human origin and the FRs of variable region and constant regions of light and heavy chains of human origin, wherein said humanized monoclonal antibody binds to human EGF-R and inhibits binding of EGF to EGF-R. According to a preferred embodiment of the humanized monoclonal antibody, the hypervariable regions of the antigen binding sites comprise the amino acid sequences underlined in FIG. 1. Preferably, the FRs of the variable region which is not related to the antigen binding sites comprise the following amino acid sequences:
light chain:
FR1: asp-ile-gln-met-thr-gln-ser-pro-ser-ser-leu-ser-ala-ser-val-gly-asp-arg-val-thr-ile-thr-cys (SEQ ID NO: 1),
FR2: trp-tyr-gln-gln-thr-pro-gly-lys-ala-pro-lys-leu-leu-ile-tyr (SEQ ID NO: 2),
FR3: gly-val-pro-ser-arg-phe-ser-gly-ser-gly-ser-gly-thr-asp-phe-thr-phe-thr-ile-ser-ser-leu-gln-pro-glu-asp-ile-ala-thr-tyr-tyr-cys (SEQ ID NO: 3),
FR4: phe-gly-gln-gly-thr-lys-leu-gln-ile-thr-arg-glu (SEQ ID NO: 4),
heavy chain:
FR1: gln-val-gln-leu-gln-gln-ser-gly-ala-glu-val-lys-lys-pro-gly-ser-ser-val-lys-val-ser-cys-lys-ala-ser-gly-tyr-thr-phe-thr (SEQ ID NO: 5),
FR2: trp-val-arg-gln-ala-pro-gly-gln-gly-leu-glu-trp-ile-gly (SEQ ID NO: 6),
FR3: (arg,lys)-(val,ala)-thr-ile-thr-val-asp-glu-ser-(thr,ser)-(thr,asn)-tyr-ala-tyr-met-glu-leu-ser-ser-leu-arg-ser-glu-asp-ala-tyr-phe-cys-(ala,thr)-arg (SEQ ID NO: 7),
FR4: trp-gly-gln-gly-ser-thr-val-thr-val-ser-ser (SEQ ID NO: 8),
and wherein the amino acids listed in brackets are alternatives.

The humanized monoclonal antibody may comprise a derivative of an amino acid sequence modified by amino acid substitution within the variable and constant regions wherein the biological function of specific binding to the antigen is preserved.

In a preferred embodiment of the humanized and chimeric monoclonal antibodies of this invention, the constant region of the heavy chain comprises the amino acid sequence of a gamma-1 chain and the constant regions of the light chain comprise the amino acid sequences of a kappa chain of a human immunoglobulin. Preferred is a purified humanized or chimeric monoclonal antibody which derives from murine mAb R3.

The invention furthermore includes a pharmaceutical composition comprising a chimeric or humanized monoclonal antibody as defined herein. Usually, the composition will also contain a pharmaceutically acceptable carrier.

The invention is also embodied in the use of a humanized or chimeric antibody as defined herein for the manufacture of a drug directed to tumors, and use of a humanized or chimeric antibody as defined herein for diagnostic localization and assessing tumor growth.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 1a: Deduced aminoacid sequence of VK of murine R3 antibody. CDRs are underlined.

FIG. 1b: Deduced amino acid sequence of VH of murine R3 antibody. CDRs are underlined.

FIG. 2a: Aminoacid sequence of murine and humanized VK containing mAb R3 CDRs.

FIG. 2b: Aminoacid sequence of murine and humanized VH containing mAb R3 CDRs.

FIG. 5: Comparison of the aminoacid sequences of reshaped humanized R3 heavy chain variable region. The CDRs are underlined.

Figure 3:
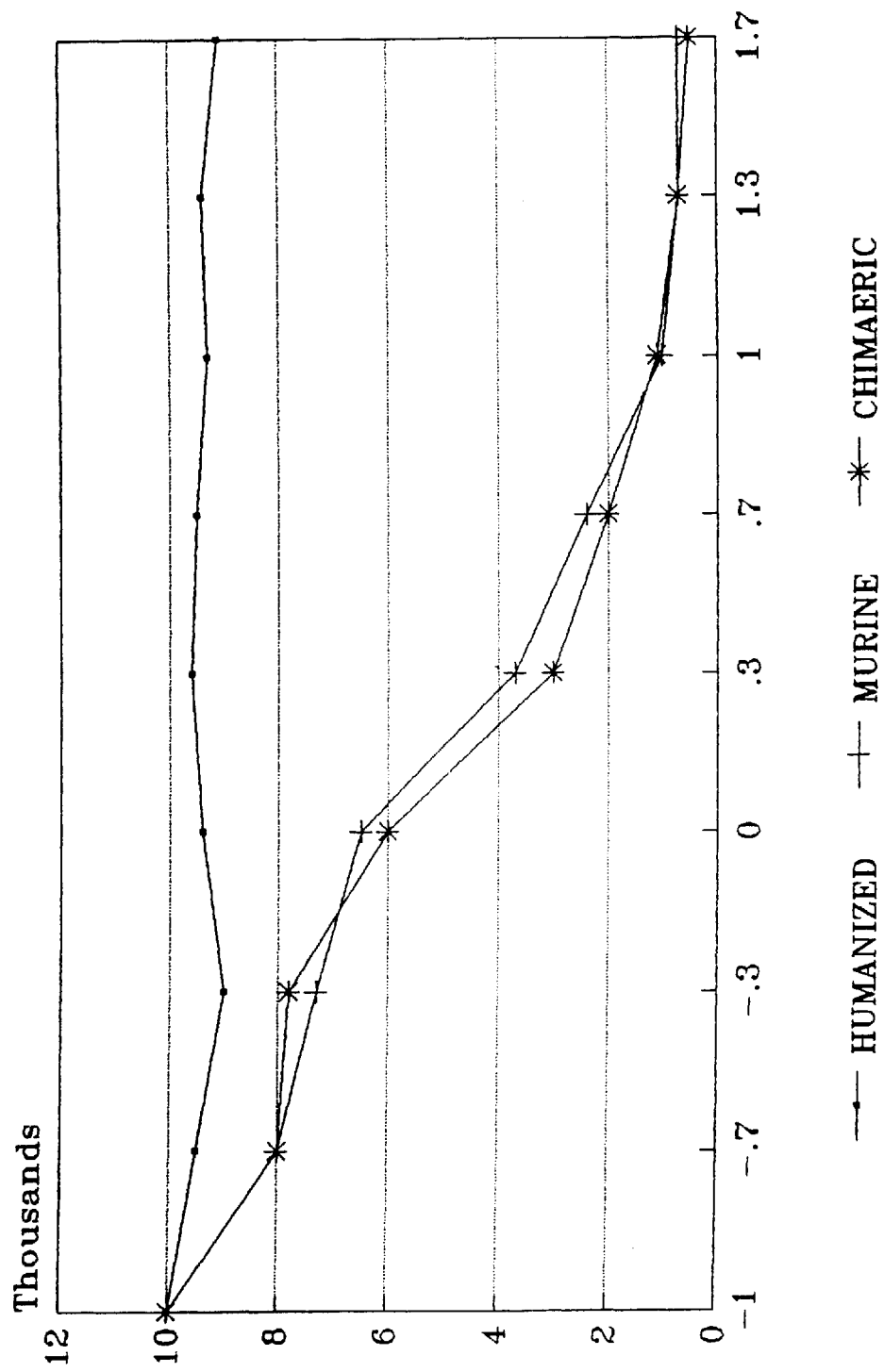
FIG. 3: Detection of binding of the chimaeric and humanized R3 to EGF-R by RRA. Antigen binding activity was assayed in different concentrations of purified murine R3 (+), chimaeric R3 (*) and humanized (1) R3 (−.−) and plotted as CPM of bound $^{125}$I-EGF against log of the concentration of each antibody. (concentration of IgG was quantitated by ELISA, see detailed description of the invention).

DETAILED DESCRIPTION OF THE INVENTION cDNA Synthesis and Gene Amplification of Variable Region of R3

Cytoplasmic RNA was extracted from about $10^6$ hybridoma cells of R3 (IgG 2A), this antibody was obtained by us (Fernandez A et al; (1989) IFN y Biotecnologia 6(3), 289–298). The method used to extract RNA was described by Faloro et al (Faloro J, Treisman R and Kemen R; (1989) Methods in Enzymology 65: 718–749).

The cDNA synthesis reaction mixture was done as described Tempest et al (Tempest P R, Bremner P, Lambert M, Taylor G, Furze J M, Carr F D J and Harris W J; (1991) Biotechnology 9: 266–271). Briefly, a 50 ul reaction mixture containing 5 ug of mRNA, 25 pmol of Vh or VK primer FOR, 250 uM of each dNTP, 10 mM DTT, 50 mM Tris-HCl (pH 8.3), 8 mM $MgCl_2$, 75 mM KCl and 15 units of RNAse inhibitor, was heated at 70° C., for 10 min and slowly cooled to 37° C. over a period of 30 min. Then, 100 units MLV reverse transcriptase (BRL) were added and the incubation at 37° C. continued for 1 hour.

The VH and VK cDNAs were amplified using the PCR as described by Orlandi et al (Orlandi R, Gussow D H, Jones P T and Winter G; (1989) Proc Natl Acad Sci USA 86: 3833–3837). For PCR amplification of VH, DNA/primers mixture consisted of 5 ul cDNA, 25 pmoles CG2AFOR and VH1BACK primers. For PCR amplification of VK, DNA/primers mixture consisted of 5 ul cDNA, 25 pmoles CK2FOR and VK10BACK primers. To these mixtures were added 2.5 mM of each dNTP, 5 ul constituents of 10× buffer thermolase and 1 unit of Thermolase (IBI) in a final volume of 50 ul. Samples were subjected to 25 thermal cycles at 94° C., 30 sec; 50° C., 30 sec; 72° C., 1 min; and a last incubation for 5 min at 72° C. Amplified VH and VK DNA were purified on Prep A Gene purification kit (BioRad).

Cloning and Sequencing of Amplified cDNA

The purified VH and VK cDNA were cloned into M13-mp19 vector. Clones were sequenced by the dideoxy method using T7 DNA Pol (Pharmacia). We reamplified the cDNA by PCR using VH1BACK and VH1FOR primers for VH and VK3BACK and VK3FOR primers for VK. The amplified cDNAs were digested with PstI and BstEII for the VH gene or PvuII and BglII for the VK gene. The fragments were cloned into M13-VHPCR1 (digested with PstI and BstEII) or into M13-VKPCR1 (digested with PvuII and BclI). The M13VHPCR-R3 and M13VKPCR-R3 containing V gene inserts were identified directly by sequencing.

Construction of Chimeric Genes

The VH gene together with the Ig heavy chain promoter, appropriated splicing sites and signal peptide sequences were excised from M13 vectors by digestion with HindIII and BamHI and cloned into an expression vector (pSVgpt). A human IgG1 constant region (Takahashi N, Veda S, Obatu M, Nikaido T, Nakai S and Honjo T; (1982) Cell 29: 718–749), was then added as a BamHI fragment. The resultant construction was R3VH-pSVgpt. The construction of the R3VK-pSVhyg was essentially the same except that the gpt gene was replaced by the hygromycin resistance gene and a human Kappa chain constant region was added (Hieter P A, Max E E, Seidman J G, Maizel J V Jr and Leder P; (1980) Cell 22: 197–207).

Chimaeric Antibody Expresion

NSO cells were electroporated with 4 ug of R3VH-pSVgpt gamma 1 region and 8 ug R3VK-pSVhyg kappa constant region were linearized by digestion with PvuI. The DNAs were mixed together, ethanol precipitated and dissolved in 25 ul water. Approximately $10^7$ NSO cells were grown to semiconfluency, harvested by centrifugation and resuspended in 0.5 ml DMEN together with the digested DNA in an electroporation cuvette. After 5 minutes on ice, the cells were given a pulse of 170 volts and 960 uF (Gene-Pulser, Bio-Rad) and left in ice for a further 30 minutes. The cells were then put into 20 ml DMEN plus 10% fetal calf serum and allowed to recover for 48 hours. At this time the cells were distributed into a 96-well plate and selective medium applied (DMEN, 10% fetal calf serum, 0.8 ug/ml mycophenolic acid, 250 ug/ml xanthine). Transfected clones were visible with the naked eye 14 days later.

The presence of human antibody in the medium of wells containing transfected clones was measured by ELISA. Microtiter plate wells were coated with goat anti-human IgG (gamma chain specific) antibodies (Sera Lab). After washing with PBST (phosphate buffered saline containing 0.02% Tween 20, pH 7.5), 20 ul of culture medium from the wells containing transfectants was added to each microtiter well for 1 hour at 37° C. The wells were then emptied, washed with PBST and peroxidase-conjugated goat anti-human Kappa, light chain specific (Sera-Lab), were added and incubated at 37° C. for one hour. The wells were then emptied, washed with PBST and substrated buffer containing o-phenylediamine added. Reactions were stopped after a few minutes by the addition of sulphuric acid and absorbance at 492 nm was measured.

Transplantation of CDRs into Human Frameworks

The construction of the first version of humanized of R3-huVH(a) and R3-huVK was carried out using a CDR grafting approach similar to that described by Kunkel et al (Kunkel T A; (1985) Proc Natl Aca Sci USA 82, 488; Kunkel T A; (1987) Methods in Enzymology 155, 166). Briefly: To 0.5 ug of VH or VK single stranded Uracil DNA in M13 VH or VK PCR vectors (coding for the human Eu VH region sequence and human REI VK region sequence) were added ten pmoles of VH or VK phosphorylated oligonucleotides encoding the mouse CDRs sequences. Primers were annealed on the template by heating to 70° C. and slowly cooled to 37° C. After site-directed mutagenesis, the DNA was transformed into competent E. coli TG1 cells. Single strand DNA was prepared from individual plaques and sequenced. If only single or double mutants were obtained, then these were subjected to further rounds of mutagenesis using the appropriated oligonucleotides until the triple CDR mutants were obtained.

Further versions of reshaped human R3VH were constructed using PCR mutagenesis (Kammann M, Laufs J, Schell J and Gronenborn B; (1989) PNAS USA 86, 4220–4224), using the oligonucleotides described in example 5.

Cloning and Expression of Humanized R3 Antibody into NSO Cells

After CDR-grafting, the HindIII-BamHI fragment carrying the R3 humanized VH and R3 humanized VK genes were recloned in expression vectors, yielding the plasmids R3HuVH(1-7)-pSVgpt gammal and HuR3VK-pSVhyg kappa constant region. Vectors were linearized with PvuI, and humanized expression was done like chimaeric expression into NSO cells.

Molecular Modelling of mAb R3 VK and VH

A model of the variable regions of mouse mAb R3 was built using the molecular modeling program QUANTA/CHARm 4.0 (Molecular Simulations Inc, 1994), running on a 150 MHz Silicon Graphics Indigo Extreme workstation.

The VK and VH frameworks were built separately from Fab 26–10 (Jeffrey P D, Strong R K, Sieker L C, Chang C Y, Campbell R L, Petsko G A, Haber E, Margolies M N and Sheriff S; (1993) PNAS USA 90, 10310) and Fab 36–71 (Strong R K, Campbell R L, Rose D R, Petsko G A, Sharon J and Margolies M N; (1993) Biochemistry 30, 3739), respectively, Fab 26–10 and mAb R3 have 92% homology in the VK frameworks and 88% homology in the whole VK region. The VH frameworks of Fab 36–71 and R3 mAb have 85% homology.

Coordinates were taken from the Brookhaven Protein Data Bank (entries 1IGI and 6FAB). The frameworks of Fab 36–71 were fitted to the frameworks of Fab 26–10, matching only those residues that have been found to be often involved in the interface between the light and heavy variable regions (Chotia C, Novotny J, Bruccolery R and Karplus M; (1985) J Mol Biol 186, 651). The VH domain of Fab 26–10 and the VK domain of Fab 36–71 were then deleted leaving the needed hybrid. Side-chain replacements were performed following the maximum overlap procedure (Snow M E and Amzel L M; (1986) Proteins 1, 267), and comparing, where possible, with other crystal structures.

The hypervariable regions of the R3-Variable Light (VL) domain (L1, L2 and L3) were built retaining the same main-chain conformations as in Fab 26–10, since the corresponding CDRs in both antibodies are highly homologous and belong to the same canonical structural groups (Chotia C, Lesk A M, Tramontano A, Levitt M, Smith-Gill S J, Air G, Sherii S, Padlan E A, Davies D, Tulip W R, Colman P M, Spinelli S, Alzari P M and Poljak R J; (1989) Nature 342, 877). In the VH domain of mAb R3, CDR H1 belongs to canonical structural group 1, as in Fab 36–71, so the main-chain torsion angles of the parent molecule were kept. CDR H2 corresponds to canonical structural group 2 and the main-chain conformation for this loop was taken from the Fv fragment 4D5 (entry 1FVC), which was selected among other highly resolved structures because of the good matching of its H2 loop base with the framework of Fab 36–71. For all the above mentioned loops comparisons with other CDRs from the Data Bank were made to orient the side chains.

To model CDR H3, which in mAb R3 was 14 amino acids long, a high temperature molecular dynamics was used for conformational sampling (Bruccoleri R E and Karplus M; (1990) Biopolymers 29, 1847). First, the whole structure without CDR H3 was subjected to an energy minimization keeping residues H-94 and H-103 fixed and using harmonic constraints of 10 Kcal/(mole atom $A^2$) for main chain atoms. Then a loop was constructed with an arbitrary conformation starting from the two previously fixed amino acids. Those residues close to the framework were placed taking into consideration other crystal structures and the top part of the loop was built with an extended conformation avoiding strong steric interactions with the rest of the molecule. For the next modeling steps only CDR H3 and the neighboring side chains within a distance of $5A^0$ were permitted to move. An energy minimization was first carried out and then a molecular dynamics at 800K was run for 150 picoseconds. The time step for the run was set to 0.001 picosecond and coordinates were saved every 100 steps. The 120 lowest energy conformations from the dynamics run were extracted and subjected to an energy minimization in which all atoms in the structure were allowed to move. Several low-energy conformations were obtained and the one with the lowest energy was used in the subsequent analyses. Differences between murine and humanized variants of R3 antibody were individually modeled to investigate their possible influence on CDR conformation.

EGF Receptor Radioligand Competition Assays

The determination of the apparent inhibition constants (Ki) of the $^{125}$I-EGF binding to its receptor by the anti EGF-R mAb was performed by an homogeneous Radio Receptor Analysis (RRA) with human placenta microsomal fraction (Macias A, Pérez R, Lage A; (1985) Interferon y Biotecnología 2: 115–127). The affinity constant of the antigen antibody reaction was estimated also by a competitive RRA but using mAb $^{125}$I-R3 as the radiolabelled probe.

Materials

Recombinant Human Epidermal Growth Factor (hEGF) was obtained from the Center of Genetic Engineering and Biotechnology, Havana, Cuba. $^{125}$I-hEGF was radioiodinated by the chloramine-T method (specific activity 150–200 uCi/ug). Murine hybridoma cell line R3 was obtained by us (European Patent Application No 93202428.4). Rat myeloma NSO is a non-Ig secreting cell line and was grown in Dulbecco's modified Eagles medium (DMEN) containing 10% fetal calf serum. Vectors M13VHPCR1, M13VKPCR1, pSVgpt and pSVhyg have been described in detail (Orlandi R, Gussow D H, Jones P T and Winter G; (1989) Proc Natl Acad Sci USA 86: 3833–3837) and were obtained from Greg Winter, MRC Laboratory of Molecular Biology, Cambridge, UK. Oligonucleotides were synthesized using an Applied Biosystems 381 DNA synthesizer.

Pharmaceutical Compositions

With respect to the formulation of suitable compositions for administration to patients in need of treatment, the monoclonal antibodies according to the invention may be admixed or combined with pharmaceutically acceptable carriers known per se, dependent upon the chosen route of administration. There are no particular limitations to the modes of application of the invention, and the choice of suitable administration routes and suitable compositions belong to the routine skills of persons skilled in the art.

Although other forms of administration are possible as well, a preferred administration form would be a solution for injection, in particular for intravenous or intraarterial injection. Usually, a suitable pharmaceutical composition for injection may comprise a buffer (e.g. acetate, phosphate or citrate buffer), a surfactant (e.g. polysorbate), optionally a stabilizer agent (e.g. human albumine), etc. Persons skilled in the art know, or can easily determine, other possibilities.

Similarly, persons skilled in the art have the ability to determine the best concentrations and proportions of the various components, administration dose and frequency, etc. For example, a suitable solution for injection will usually contain from about 1 to about 20, preferably 5–10 mg antibody per ml. The dose to be administered could for example be from about 0.1 to about 20, preferably 1–5 mg/kg body weight, and administration could be once per day, or three times per week, or whatever the physician thinks best.

EXAMPLE 1

Molecular Cloning Sequencing

VH and VK were amplified using PCR. The specific oligonucleotides used as primers were:

For the heavy chain variable region:

CG2AFOR (5' GGAAGCTTAGACCGATGGGGCCT-GTTGTTTTG 3') (SEQ ID NO: 9);

VH1BACK (5' AGGT(G/C)(A/C)A(A/G)CTGCAG(G/C)AGTC(A/T)GG 3') (SEQ ID NO: 10).

For the light chain variable region:

CK2FOR (5' GAAGCTTGAAGATGGATACAGTTG-GTGCAGC 3') (SEQ ID NO: 11);

VK10BACK (5' TTGAATTCCAGTGATGTTTTGAT-
GACCCA 3') (SEQ ID NO: 12).

Figures 1A, 1B, 2A, 2B:
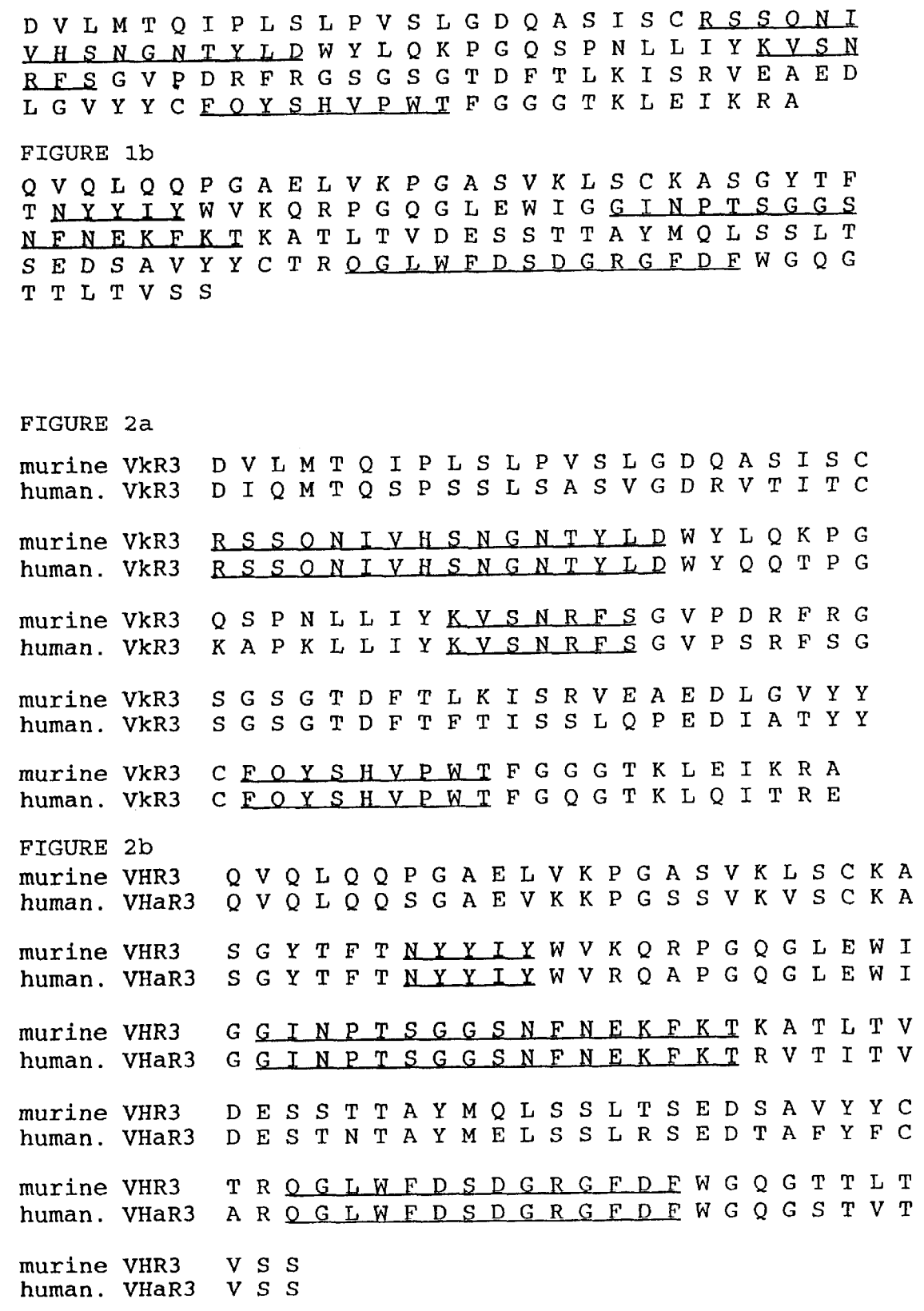

The purified VH and VK cDNA were cloned into M13 vector. Twelve independent clones were sequenced by the dideoxy method using T7 DNA Pol (Pharmacia). In FIG. 1, you can see the variable region sequences of the murine R3 mAb. The VH sequence is most closely related to kabat subgroup VH IIB and the VK to kabat subgroup II.

EXAMPLE 2
Construction of Chimeric Genes

We reamplified the cDNA by PCR using the following oligonucleotides as primers:

For VH:
VH1BACK (5' AGGT(G/C)(A/C)A(A/G)CTGCAG(G/C)AGTC(A/T)GG 3') (SEQ ID NO: 10);

VHb 1FOR (5' TGAGGAGACGGTGACCGTGGTC-CCTTGGCCCCAG 3') (SEQ ID NO: 13).

For Vk:
VK3BACK (5' GACATTCAGCTGACCCA 3') (SEQ ID NO: 14);

VK3FOR (5' GTTAGATCTCCAGTTTGGTGCT 3') (SEQ ID NO: 15).

The amplified cDNAs were digested with PstI and BstEII for the VH gene or PvuII and BglII for the VK gene. The fragments were cloned into M13-VHPCR1 (digested with PstI and BstEII) or into M13-VKPCR1 (digested with PvuII and BclII). Details of vectors (Orlandi R et al; Proc Natl Acad Sci USA 86: 3833–3837, 1989). The M13VHPCR-R3 and M13VKPCR-R3 containing V gene inserts were identified directly by sequencing.

The VH gene together with the Ig heavy chain promoter, appropriated splicing sites and signal peptide sequences were excised from M13 vectors by digestion with HindIII and BamHI and cloned into an expression vector (pSVgpt). A human IgG1 constant region (Takahashi N et al; Cell 29: 718–749, 1982) was then added as a BamHI fragment. The resultant construction was R3VH-pSVgpt. The construction of the R3VK-pSVhyg was essentially the same, except that the gpt gene was replaced by the hygromycin resistance gene and a human Kappa chain constant region was added (Hieter PA et al; Cell 22: 197–207, 1980).

EXAMPLE 3
Transplantation of Murine CDRs of R3 into Human FRs

We compared murine light and heavy chains variable regions of R3 with variable regions sequences of human immunoglobulins.

The murine R3 heavy chain variable region has 63.4% of homology with human subgroup VHI and the R3 light chain variable region has 63.7% of homology with human subgroup VKI. The human FRs choosen were derived of the human immunoglobulin REI for the light chain and the human immunoglobulin EU for the heavy chain.

The construction of the first version of the humanized R3 heavy chain and humanized R3 light chain was carried out using CDR grafting approach as described in Detailed description of the invention.

Oligonucleotides were designed which consisted of DNA sequences coding for each end by 12 bases of DNA complementary to the DNA sequences coding for the adjacent FRs of human Eu for Vh and human REI for VK.

The oligonucleotides designed were:
For the CDR1 of the light chain:
5' TCTAGATCAGTCTTGTAACATGTATCAT-TACCTTTGTGGATAAATCTG 3' (SEQ ID NO: 16).

We didn't use oligonucleotides for the CDR2 because REI human CDR2 is identical to R3 CDR2.

For the CDR3 of the ligh chain:
5' GATGACGAAAGTTATCAAGTGTACAAGG-GACCTG 3' (SEQ ID NO: 17).

For the CDR1 of the heavy chain:
5' ATGTGGAAGTGGTTAATAATATA-GATAACCCACTCTGTC 3' (SEQ ID NO: 18).

For the CDR2 of the heavy chain:
5' ACTACCTACCCTCCCTATTTGGGGTG-GAGACCTCCCTCATTGAAAT-TACTTTTCAGTTCTGTTCTCACTGTTAA 3' SEQ ID NO: 19).

For the CDR 3 of the heavy chain:
5' AAAACACGTTCTGTCCCGAACAC-CAAGCTGTCACTGCCTGCCCCGAAACTGAAG 3' (SEQ ID NO: 20).

EXAMPLE 4
Expression of Chimeric and Humanized in NSO Cells

NSO cells were electroporated with 4 ug of murine or humanized R3VH-CMMAR gamma 1 region and 8 ug of murine or humanized R3VK-CMMARhyg kappa constant region were linearized by digestion with PvuI. The DNAs were mixed together, ethanol precipitated and dissolved in 25 ul water. Approximately $10^7$ NSO cells were grown to semiconfluency, harvested by centrifugation and resuspended in 0.5 ml DMEN together with the digested DNA in an electroporation cuvette. After 5 minutes on ice, the cells were given a pulse of 170 volts and 960 uF (Gene-Pulser, Bio-Rad) and left in ice for a further 30 minutes. The cells were put into 20 ml DMEN plus 10% fetal calf serum and allowed to recover for 48 hours. At this time the cells were distributed into 96-well plate and selective medium applied (DMEN, 10% fetal calf serum, 0.8 ug/ml mycophenolic acid, 250 ug/ml xanthine). Transfected clones were visible with the naked eye 14 days later.

The presence of human antibody in the medium of wells containing transfected clones was measured by ELISA. Microtiter plate wells were coated with goat anti-human IgG (gamma chain specific) antibodies (Sera Lab). After washing with PBST (phosphate buffered saline containing 0.02% Tween 20, pH 7.5), 20 ul of culture medium from the wells containing transfectants was added to each microtiter well for 1 hour at 37° C. The wells were then emptied, washed with PBST and peroxidase-conjugated goat anti-human Kappa, light chain specific (Sera-Lab), were added and incubated at 37° C. for one hour. The wells were then emptied, washed with PBST and substrated buffer containing o-phenylenediamine added. Reactions were stopped after a few minutes by the addition of sulphuric acid and absorbance at 492 nm was measured.

In FIG. 3 you can see that the chimeric and murine R3 antibody bind to the EGF-R with the same affinity (tested in RRA), and the first version of humanized R3 antibody didn't bind to the EGF-R.

EXAMPLE 5
Construction of Different Versions of Humanized R3 Antibodies, with Some Murine Residues in the FRs Regions The introduction of some murine residues in the human FRs was necessary because the first version of humanized that we constructed didn't bind to the antigen.

Figure 4:
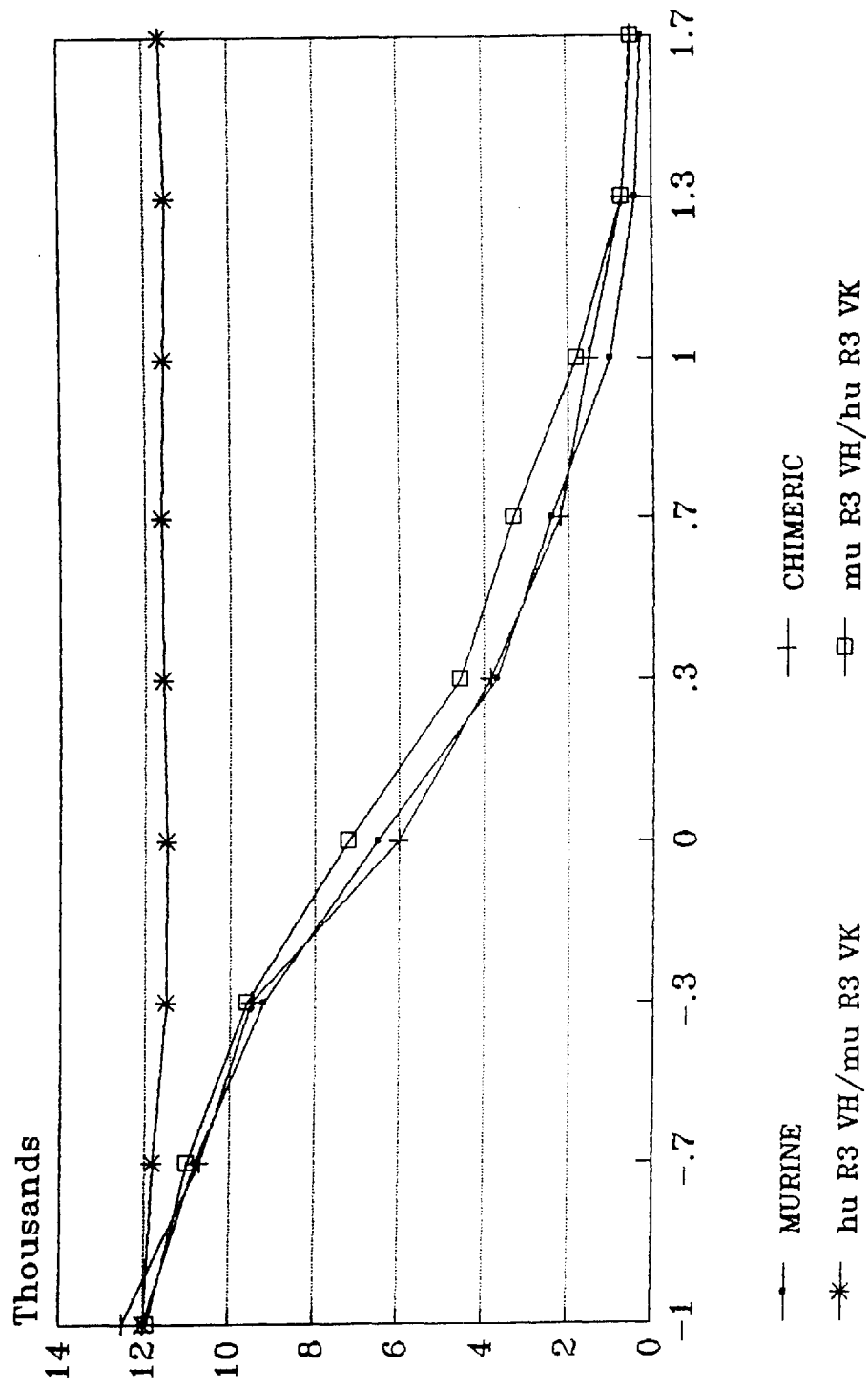
FIG. 4: Detection of binding of hybrids murine R3 VH/humanized R3 VK and humanized R3 VH/murine R3 VK. The antigen binding activity was assayed in dilutions concentrated supernatants from transfected NSO cells and plotted as cpm (membrane bound radioactivity) against log of the concentration of IgG estimated by ELISA, see experimental protocols.

We constructed hybrids between murine R3VH/humanized R3VK and humanized R3VH/murine R3VK. FIG. 4 shows that the hybrid murine R3VH/humanized R3VK binds to the EGF-R with the same affinity of original murine R3.

Humanized R3huVk retained all the Vernier's residues of murine R3VK. This fact may explain why the humanizing procedure did not affect the binding capability of the kappa chain.

Nevertheless humanized R3VH/murine R3VK didn't work. This result suggested us that we had to include murine residues into human FRs of the heavy chain, for the recovery of the binding to the antigen of this antibody.

Then, other versions of the reshaped humanized heavy chains were constructed by PCR mutagenesis. In these new versions we tried to remain intact the Vernier's zone, recommending changes in the position 66, 67, 75, 76 and 93 in the FRs regions.

The oligonucleotides designed to get the reshaped R3VH-K66A67 were:
Top strand:
5' GAAAAGTTCAAGACAAAAGCGACAAT-TACGGTAGAC 3' (SEQ ID NO: 21).
Lower strand:
5' GTCTACCGTAATTGTCGCTTTTGTCT-TGAACTTGAACTTTTC 3' (SEQ ID NO: 22).

The oligonucleotides designed to get the reshaped R3VH-S75T76 were:
Top strand:
5' GTAGACGAGAGCAGCACCACGGCGTACATG 3' (SEQ ID NO: 23).
Lower strand:
5' CATGTACGCCGTGGTGCTGCTCTCGTCTAC 3' (SEQ ID NO: 24).

The oligonucleotides designed to get the reshaped R3VH-T93 were:
Top strand:
5' TTCTATTTTTGTACAAGACAGGGCTTG 3' (SEQ ID NO: 25).
Lower strand:
5' CAAGCCCTGTCTTGTACAAAAATAGAA 3' (SEQ ID NO: 26).

EXAMPLE 6
Molecular Modelling of mAb R3 VK and VH

A model of the variable regions of mouse mAb R3 was built using the molecular modeling program QUANTA/CHARm 4.0 (Molecular Simulations Inc, 1994), running on a 150 MHz Silicon Graphics Indigo Extreme workstation.

Differences between murine and humanized variants of R3 antibody were individually modeled to investigate their possible influence on CDR conformation.

Figure 6:
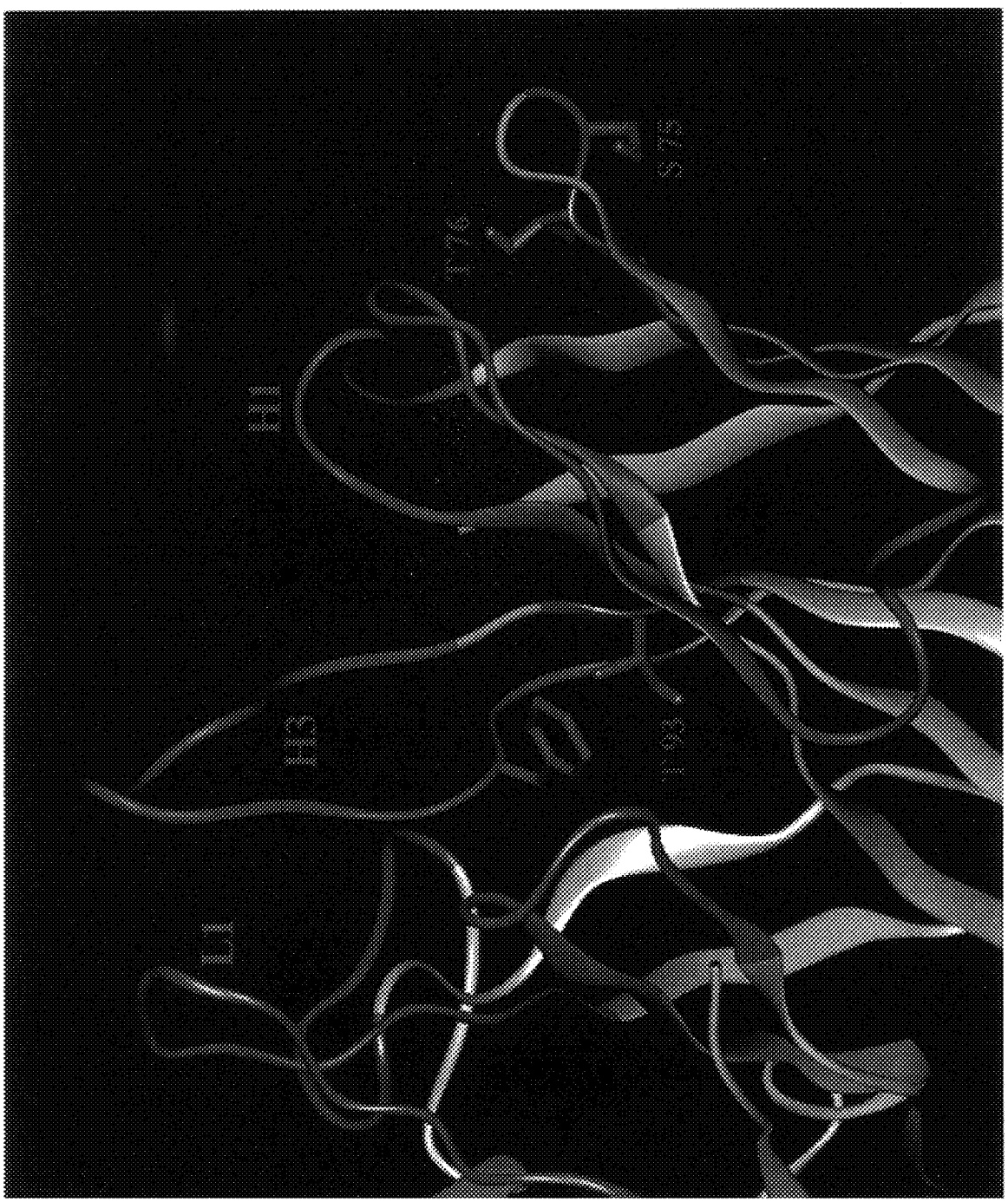
FIG. 6: Molecular Model of the Variable region of murine mAb R3. The binding site is at the top and the molecule has been slightly rotated clockwise around a vertical axis so that VH domain approaches the viewer. The VL framework is light blue and the VH framework is pink. The corresponding CDRs are marked in dark blue and red. Side chains of residue Ser 75, Thr 76 and Thr 93 (with polar hydrogen atoms included) are shown in green. The side chain of the Phe 100f is shown in red.

Heavy chain variable region residues at positions 66, 67, 75, 76 and 93, which had been changed in humanized R3huVH (FIG. 6), are close to the hypervariable loops and therefore may influence the CDR conformations. Both our experimental results and the modeling studies suggest that only Thr76 and Thr93 are critical for binding affinity.

A molecular model of the murine R3 heavy chain variable regions was constructed to analyze the possible effects of these mutations. Residue 93 was located just below CDR H3, close to Phe100f (FIG. 6), and replacing Thr by a smaller amino acid like Ala may provoke some rearrangements of the neighboring side chains and modify the overall conformation of the H3 loop.

THR 76 as close to CDR H2 (FIG. 2) and the introduction of the larger Asn residue as this position could lead to hydrogen-bonding interactions with the backbone of CDR H1. Moreover, residue 76 is accessible from the top of the variable region and could be directly involved in the binding to EGF-R. The substitution Ser75—Thr alone did not seem to have any influence, but taken together with mutation at position 76, it could be important. The changes Lys66—Arg and Ala67—Val were not seen to affect the structure, but since they had been found to have some influence in the functional binding of reshaped mAb 425 (Kettleborough C, Saldanha J, Heath V J, Morrison C J and Bending M M; (1991) Protein Engineering 4, 773–783), we decided to make substitutions at these positions as well.

Humanized R3huVK retained all the Vernier's residues of murine R3VK. This fact may explain why the humanizing procedure did not affect the binding capability of the kappa chain.

Figure 7:
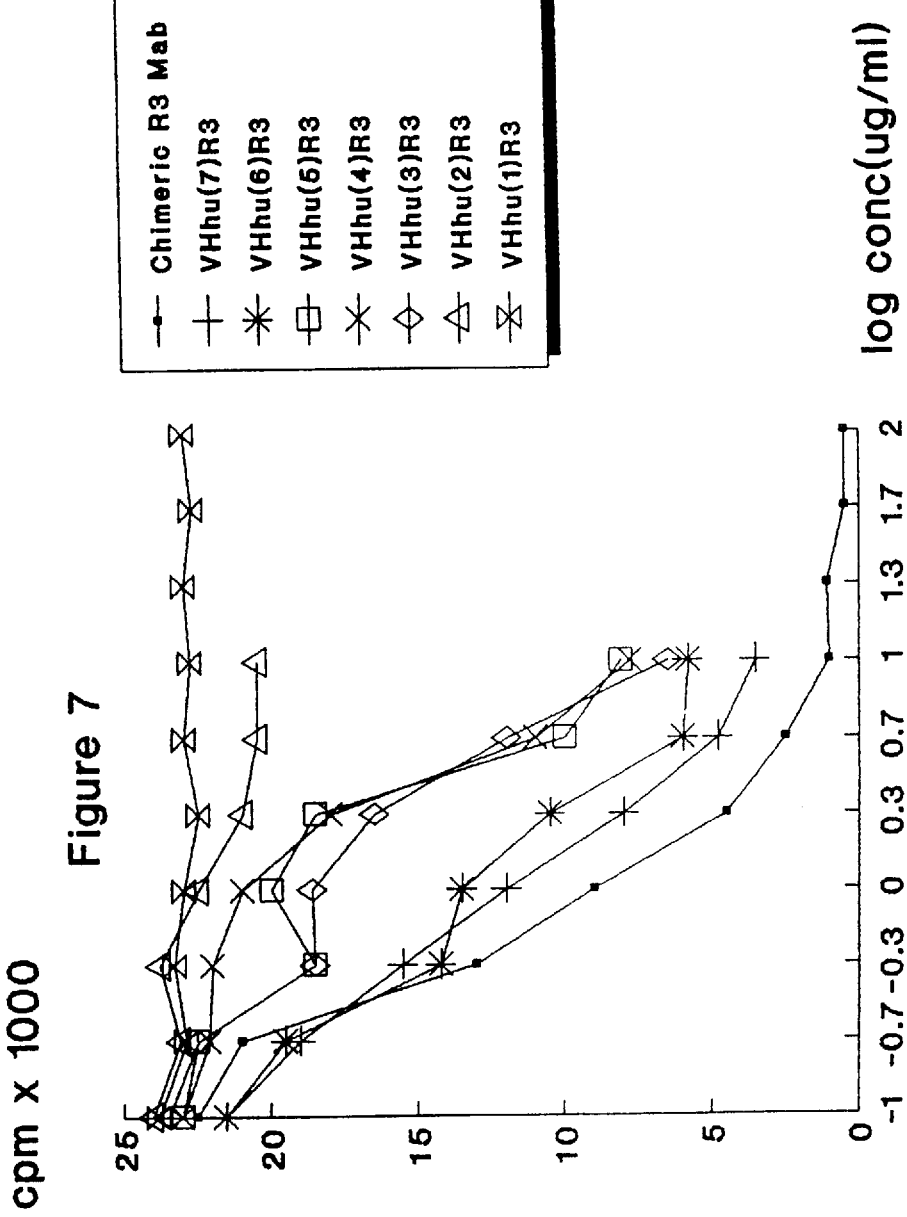
FIG. 7: Detection of binding of the different reshaped mAb R3 to EGF-R by RRA. Antigen binding activity was assayed in dilutions concentrated supernatants from transfected NSO cells and plotted as cpm (membrane bound radioactivity) against log of the concentration of IgG estimated by ELISA, see experimental protocols. All versions of reshaped human VH regions were cotransfected with huVKR3 and are represented in the figure.

Reshaped R3 hu VH antibodies containing either S75/T76 or T93 recovered partially the binding capacity, whereas those constructs containing both of them retained full binding activity (FIG. 7).

EXAMPLE 7
EGF Receptor Radioligand Competition Assays

The determination of the affinity constant of the $^{125}$I-EGF binding to its receptor by murine R3, chimeric and humanized antibodies was performed by an homogeneous Radio Receptor Analysis (RRA) with human placenta microsomal fraction (Macias A et al; Interferon y Biotecnología 2: 115–127, 1985).

These chimeric and humanized different versions antibodies were assayed using this technique for its ability to bind to EGF-R (FIG. 7). As you can see the different versions of reshaped human VH regions result in a wide variety of levels of antigen binding (FIG. 7). Versions 6 and 7 have the same affinity of original murine antibody, these versions with highest levels of binding were followed of versions 3, 4 and 5 and then followed by version 2.

Based on these results, it is possible to comment on the relative contributions of individual residues in the FRs make to antigen binding. The 75 and 76 changes are together with 93 very important to the binding, while the introduction of 66 and 67 changes fail to produce significant antigen binding.

EXAMPLE 8
Immunization of Cercopithecus Aethiops Monkeys with the Murine, Chimeric and VH Mutant Antibodies Three treatment groups with two cercopithecus aethiops monkeys in each group were immunized as follows: 1.—Murine R3 monoclonal antibody (2 mg) with 5 mg of aluminum hydroxide as adjuvant; 2.—Chimeric R3 antibody (2 mg) with 5 mg of aluminum hydroxide as adjuvant; and 3.—Humanized (version 6) R3 antibody (2 mg) with 5 mg of aluminum hydroxide as adjuvant. All the groups were immunized intradermically on weeks 1, 3, 5, and 7. Starting on week one, blood was collected from all the groups weekly.

The serum obtained and the titer of antibodies against EGF-R was determined by an ELISA technique.

Costar plates (Inc, high binding) were coated with murine R3 monoclonal antibody at a concentration of 10 ug/ml in bicarbonate buffer (pH 9.6) and incubated overnight. After, the plates were washed with PBST, were blocked with the same buffer containing 1% BSA during one hour at room temperature.

Washing step was repeated and 50 ul/well of the different serum dilutions were added. After incubating for 2 hours at 37° C., the plates were washed again and incubated 1 hour at 37° C. with alkaline phosphated conjugated goat anti-human total or anti-human IgG Fc region specific antiserum (Sigma, Inc). After washing with PBST the wells were incubated with 50 ul of substrate buffer (1 mg/ml of p-nitrophenylphosphate diluted in diethanolamine buffer (pH 9.8) and absorbance at 405 nm was read with an ELISA reader (Organon Teknika, Inc).

Figure 8:
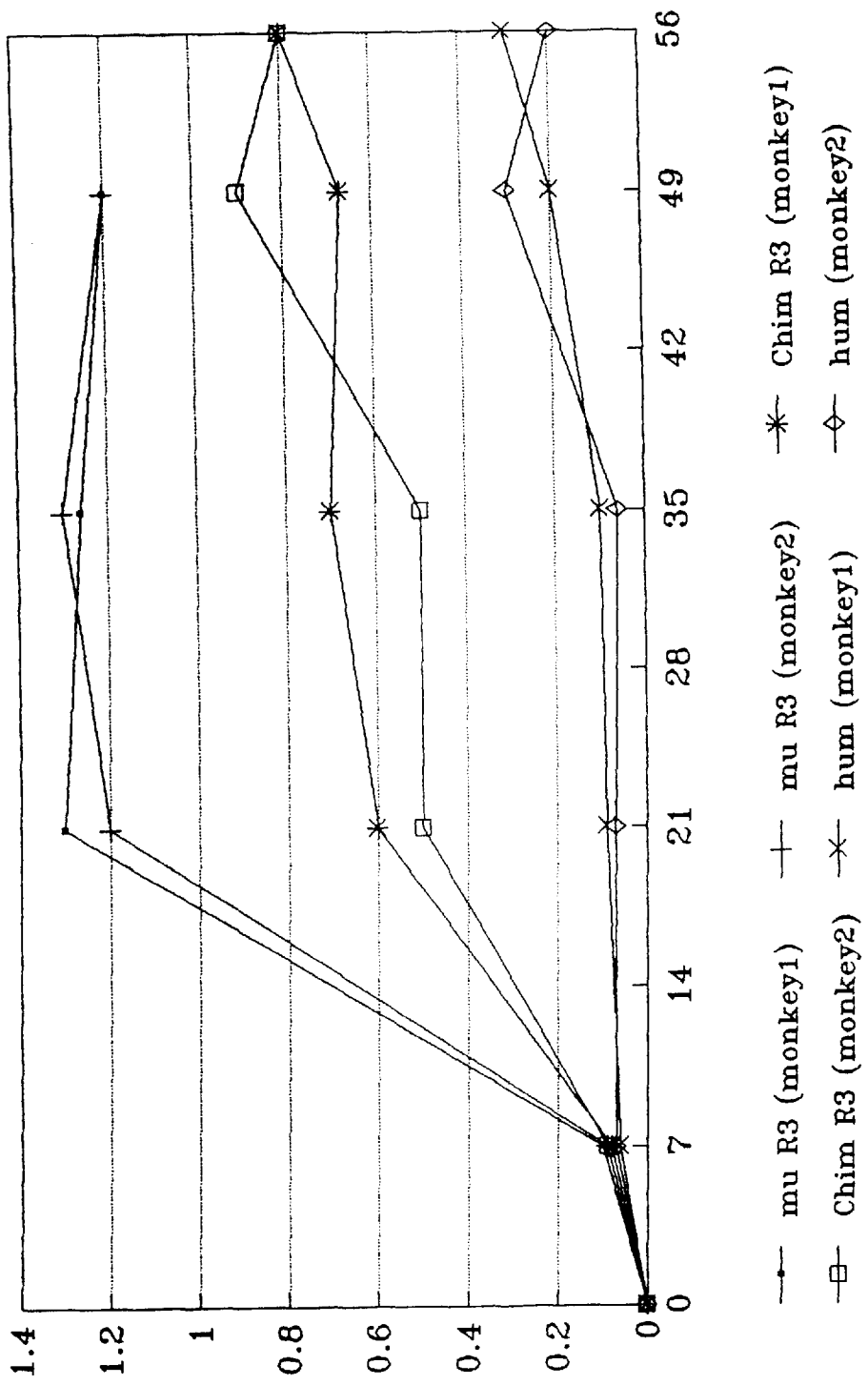
FIG. 8: Immunogenicity in monkeys of R3 murine mAb and different recombinant versions. Cercopithecus aethiops monkeys were immunized intradermically at 15 days intervals with 2 mg of the different mAbs versions using aluminium hydroxide as adjuvant. The detection of monkey IgG against the different versions of R3 mAb was tested in the sera of the animals using an indirect ELISA.

A high IgG response to murine R3 antibody was obtained when this antibody was used as immunogen. A lower but still measurable IgG response (¹/₁₀₀₀₀) to the murine R3 antibody was obtained when monkeys were immunized with the chimeric antibody, contrary to the results obtained with the humanized (version 6), (FIG. 8). With the humanized antibody no response was measurable after 3 immunizations.

DEPOSIT

The cell line hr-R3 expressing the antibody was deposited pursuant to the Budapest Treaty with European Collection of Animal Cell Cultures, Centre for Applied Microbiology and Research Microbiological, Porton Down, Salisbury Wiltshire SP4, OJG, United Kingdom on Nov. 10, 1995, and obtained deposit number 951110101.

We claim:

1. A monoclonal antibody which specifically binds epidermal growth factor receptor (EGF-R), the monoclonal antibody comprising a chimeric antibody including variable regions of non-human origin and constant regions of light and heavy chains, said constant region being of human origin, wherein the variable regions of antigen binding sites of the antibody comprise an amino acid sequence selected from the group consisting of (SEQ. ID NO. 27, SEQ ID NO. 28, SEQ ID NO. 29, SEQ ID NO. 30, SEQ ID NO. 31, SEQ ID NO. 32, SEQ ID NO. 33 and SEQ ID NO. 34.

2. A monoclonal antibody which specifically binds epidermal growth factor receptor (EGF-R), the monoclonal antibody comprising a humanized antibody including complementary determining regions of non-human origin, variable regions having framework regions (FRs) of human origin, and constant regions of light and heavy chains, said constant regions being of human origin, wherein the complementary determining regions (CDRs) comprise an amino acid sequence selected from the group consisting of SEQ ID NO 29, SEQ ID NO 30, SEQ ID NO 31, SEQ ID NO 32, SEQ ID NO 33 and SEQ ID NO 34.

3. A monoclonal antibody which specifically binds the epidermal growth factor receptor (EGF-R) where said monoclonal antibody is selected from the group comprising chimeric antibodies including variable regions of non-human origin and constant regions of light and heavy chains, said constant regions being of human origin; and humanized antibodies including complementary determining regions of non-human origin, variable regions having framework regions (FRs) of human origin, and constant regions of light and heavy chains, said constant regions being of human origin, the monoclonal antibody comprising a humanized antibody ECACC 951110101.

4. A monoclonal antibody according to claim 2 comprising a humanized monoclonal antibody, wherein the framework regions (FRs) of the variable region which is not related to the antigen binding sites comprise amino acid sequences: SEQ ID NO. 1, SEQ ID NO. 2, SEQ ID NO. 3, SEQ ID NO. 4, SEQ ID NO. 5 and SEQ ID NO. 6, SEQ ID NO. 7, SEQ ID NO. 8.

5. A pharmaceutical composition comprising the monoclonal antibody of claim 1 in admixture with a pharmaceutically acceptable carrier.

6. A pharmaceutical composition comprising the monoclonal antibody of claim 2 in admixture with a pharmaceutically acceptable carrier.

7. A pharmaceutical composition comprising the monoclonal antibody of claim 3 in admixture with a pharmaceutically acceptable carrier.

8. A pharmaceutical composition comprising the monoclonal antibody of claim 4 in admixture with a pharmaceutically acceptable carrier.

* * * * *

SEQUENCE LISTING ( 1 ) GENERAL INFORMATION:

( i i i ) NUMBER OF SEQUENCES: 34

( 2 ) INFORMATION FOR SEQ ID NO: 1:

( i ) SEQUENCE CHARACTERISTICS:
  ( A ) LENGTH: 23 amino acids
  ( B ) TYPE: amino acid
  ( C ) STRANDEDNESS: unknown
  ( D ) TOPOLOGY: unknown ( i i ) MOLECULE TYPE: protein ( i i i ) HYPOTHETICAL: NO ( x i ) SEQUENCE DESCRIPTION: SEQ ID NO: 1:

```
Asp  Ile  Gln  Met  Thr  Gln  Ser  Pro  Ser  Ser  Leu  Ser  Ala  Ser  Val
1                   5                        10                       15

Gly  Asp  Arg  Val  Thr  Ile  Thr  Cys
                    20
```

( 2 ) INFORMATION FOR SEQ ID NO: 2:

( i ) SEQUENCE CHARACTERISTICS:
  ( A ) LENGTH: 15 amino acids
  ( B ) TYPE: amino acid
  ( C ) STRANDEDNESS: unknown
  ( D ) TOPOLOGY: unknown ( i i ) MOLECULE TYPE: protein ( i i i ) HYPOTHETICAL: NO ( x i ) SEQUENCE DESCRIPTION: SEQ ID NO: 2:

```
Trp  Tyr  Gln  Gln  Thr  Pro  Gly  Lys  Ala  Pro  Lys  Leu  Leu  Ile  Tyr
1                   5                        10                       15
```

( 2 ) INFORMATION FOR SEQ ID NO: 3:

( i ) SEQUENCE CHARACTERISTICS:
  ( A ) LENGTH: 32 amino acids
  ( B ) TYPE: amino acid
  ( C ) STRANDEDNESS: unknown
  ( D ) TOPOLOGY: unknown ( i i ) MOLECULE TYPE: protein ( i i i ) HYPOTHETICAL: NO ( x i ) SEQUENCE DESCRIPTION: SEQ ID NO: 3:

```
Gly  Val  Pro  Ser  Arg  Phe  Ser  Gly  Ser  Gly  Ser  Gly  Thr  Asp  Phe
1                   5                        10                       15

Thr  Phe  Thr  Ile  Ser  Ser  Leu  Gln  Pro  Glu  Asp  Ile  Ala  Thr  Tyr
                    20                       25                       30

Tyr  Cys
```

( 2 ) INFORMATION FOR SEQ ID NO: 4:

( i ) SEQUENCE CHARACTERISTICS:
 ( A ) LENGTH: 12 amino acids
 ( B ) TYPE: amino acid
 ( C ) STRANDEDNESS: unknown
 ( D ) TOPOLOGY: unknown ( i i ) MOLECULE TYPE: protein ( i i i ) HYPOTHETICAL: NO ( x i ) SEQUENCE DESCRIPTION: SEQ ID NO: 4:

Phe Gly Gln Gly Thr Lys Leu Gln Ile Thr Arg Glu
1               5                   10

( 2 ) INFORMATION FOR SEQ ID NO: 5:

( i ) SEQUENCE CHARACTERISTICS:
  ( A ) LENGTH: 30 amino acids
  ( B ) TYPE: amino acid
  ( C ) STRANDEDNESS: unknown
  ( D ) TOPOLOGY: unknown ( i i ) MOLECULE TYPE: protein ( i i i ) HYPOTHETICAL: NO ( x i ) SEQUENCE DESCRIPTION: SEQ ID NO: 5:

Gln Val Gln Leu Gln Gln Ser Gly Ala Glu Val Lys Lys Pro Gly
1               5                   10                  15

Ser Ser Val Lys Val Ser Cys Lys Ala Ser Gly Tyr Thr Phe Thr
                20                  25                  30

( 2 ) INFORMATION FOR SEQ ID NO: 6:

( i ) SEQUENCE CHARACTERISTICS:
  ( A ) LENGTH: 14 amino acids
  ( B ) TYPE: amino acid
  ( C ) STRANDEDNESS: unknown
  ( D ) TOPOLOGY: unknown ( i i ) MOLECULE TYPE: protein ( i i i ) HYPOTHETICAL: NO ( x i ) SEQUENCE DESCRIPTION: SEQ ID NO: 6:

Trp Val Arg Gln Ala Pro Gly Gln Gly Leu Glu Trp Ile Gly
1               5                   10

( 2 ) INFORMATION FOR SEQ ID NO: 7:

( i ) SEQUENCE CHARACTERISTICS:
  ( A ) LENGTH: 32 amino acids
  ( B ) TYPE: amino acid
  ( C ) STRANDEDNESS: unknown
  ( D ) TOPOLOGY: unknown ( i i ) MOLECULE TYPE: protein ( i i i ) HYPOTHETICAL: NO ( x i ) SEQUENCE DESCRIPTION: SEQ ID NO: 7:

Arg Val Thr Ile Thr Val Asp Glu Ser Ser Thr Thr Ala Tyr Met
1               5                   10                  15

Glu Leu Ser Ser Leu Arg Ser Glu Asp Thr Ala Phe Tyr Phe Cys
                20                  25                  30

Thr Arg ( 2 ) INFORMATION FOR SEQ ID NO: 8:

( i ) SEQUENCE CHARACTERISTICS:
   ( A ) LENGTH: 11 amino acids
   ( B ) TYPE: amino acid
   ( C ) STRANDEDNESS: unknown
   ( D ) TOPOLOGY: unknown ( i i ) MOLECULE TYPE: protein ( i i i ) HYPOTHETICAL: NO ( x i ) SEQUENCE DESCRIPTION: SEQ ID NO: 8:

Trp Gly Gln Gly Ser Thr Val Thr Val Ser Ser
 1               5                   10

( 2 ) INFORMATION FOR SEQ ID NO: 9:

( i ) SEQUENCE CHARACTERISTICS:
      ( A ) LENGTH: 32 base pairs
      ( B ) TYPE: nucleic acid
      ( C ) STRANDEDNESS: unknown
      ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 9:

GGAAGCTTAG ACCGATGGGG CCTGTTGTTT TG                32

( 2 ) INFORMATION FOR SEQ ID NO: 10:

( i ) SEQUENCE CHARACTERISTICS:
      ( A ) LENGTH: 22 base pairs
      ( B ) TYPE: nucleic acid
      ( C ) STRANDEDNESS: unknown
      ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 10:

AGGTSMADCT GCAGSAGTCW GG                           22

( 2 ) INFORMATION FOR SEQ ID NO: 11:

( i ) SEQUENCE CHARACTERISTICS:
      ( A ) LENGTH: 32 base pairs
      ( B ) TYPE: nucleic acid
      ( C ) STRANDEDNESS: unknown
      ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 11:

GGAAGCTTGA AGATGGATAC AGTTGGTGCA GC                32

( 2 ) INFORMATION FOR SEQ ID NO: 12:

( i ) SEQUENCE CHARACTERISTICS:
      ( A ) LENGTH: 29 base pairs
      ( B ) TYPE: nucleic acid
      ( C ) STRANDEDNESS: unknown
      ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 12:

TTGAATTCCA GTGATGTTTT GATGACCCA 29

( 2 ) INFORMATION FOR SEQ ID NO: 13:

( i ) SEQUENCE CHARACTERISTICS:
      ( A ) LENGTH: 34 base pairs
      ( B ) TYPE: nucleic acid
      ( C ) STRANDEDNESS: unknown
      ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 13:

TGAGGAGACG GTGACCGTGG TCCCTTGGCC CCAG 34

( 2 ) INFORMATION FOR SEQ ID NO: 14:

( i ) SEQUENCE CHARACTERISTICS:
      ( A ) LENGTH: 17 base pairs
      ( B ) TYPE: nucleic acid
      ( C ) STRANDEDNESS: unknown
      ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 14:

GACATTCAGC TGACCCA 17

( 2 ) INFORMATION FOR SEQ ID NO: 15:

( i ) SEQUENCE CHARACTERISTICS:
      ( A ) LENGTH: 22 base pairs
      ( B ) TYPE: nucleic acid
      ( C ) STRANDEDNESS: unknown
      ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 15:

GTTAGATCTC CAGTTTGGTG CT 22

( 2 ) INFORMATION FOR SEQ ID NO: 16:

( i ) SEQUENCE CHARACTERISTICS:
      ( A ) LENGTH: 48 base pairs
      ( B ) TYPE: nucleic acid
      ( C ) STRANDEDNESS: unknown
      ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 16:

TCTAGATCAG TCTTGTAACA TGTATCATTA CCTTTGTGGA TAAATCTG 48

( 2 ) INFORMATION FOR SEQ ID NO: 17:

( i ) SEQUENCE CHARACTERISTICS:
      ( A ) LENGTH: 34 base pairs
      ( B ) TYPE: nucleic acid
      ( C ) STRANDEDNESS: unknown
      ( D ) TOPOLOGY: unknown (i i) MOLECULE TYPE: other nucleic acid (i i i) HYPOTHETICAL: NO (x i) SEQUENCE DESCRIPTION: SEQ ID NO: 17:

GATGACGAAA GTTATCAAGT GTACAAGGGA CCTG 34

(2) INFORMATION FOR SEQ ID NO: 18:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (i i) MOLECULE TYPE: other nucleic acid (i i i) HYPOTHETICAL: NO (x i) SEQUENCE DESCRIPTION: SEQ ID NO: 18:

ATGTGGAAGT GGTTAATAAT ATAGATAACC CACTCTGTC 39

(2) INFORMATION FOR SEQ ID NO: 19:

(i) SEQUENCE CHARACTERISTICS:
        (A) LENGTH: 74 base pairs
        (B) TYPE: nucleic acid
        (C) STRANDEDNESS: unknown
        (D) TOPOLOGY: unknown (i i) MOLECULE TYPE: other nucleic acid (i i i) HYPOTHETICAL: NO (x i) SEQUENCE DESCRIPTION: SEQ ID NO: 19:

ACTACCTACC CTCCCTATTT GGGGTGGAGA CCTCCCTCAT TGAAATTACT TTTCAGTTCT 60

GTTCTCACTG TTAA 74

(2) INFORMATION FOR SEQ ID NO: 20:

(i) SEQUENCE CHARACTERISTICS:
        (A) LENGTH: 54 base pairs
        (B) TYPE: nucleic acid
        (C) STRANDEDNESS: unknown
        (D) TOPOLOGY: unknown (i i) MOLECULE TYPE: other nucleic acid (i i i) HYPOTHETICAL: NO (x i) SEQUENCE DESCRIPTION: SEQ ID NO: 20:

AAAACACGTT CTGTCCCGAA CACCAAGCTG TCACTGCCTG CCCCGAAACT GAAG 54

(2) INFORMATION FOR SEQ ID NO: 21:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (i i) MOLECULE TYPE: other nucleic acid (i i i) HYPOTHETICAL: NO (x i) SEQUENCE DESCRIPTION: SEQ ID NO: 21:

GAAAAGTTCA AGACAAAAGC GACAATTACG GTAGAC 36

( 2 ) INFORMATION FOR SEQ ID NO: 22:

( i ) SEQUENCE CHARACTERISTICS:
        ( A ) LENGTH: 42 base pairs
        ( B ) TYPE: nucleic acid
        ( C ) STRANDEDNESS: unknown
        ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 22:

GTCTACCGTA ATTGTCGCTT TTGTCTTGAA CTTGAACTTT TC 42

( 2 ) INFORMATION FOR SEQ ID NO: 23:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 23:

GTAGACGAGA GCAGCACCAC GGCGTACATG 30

( 2 ) INFORMATION FOR SEQ ID NO: 24:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 24:

CATGTACGCC GTGGTGCTGC TCTCGTCTAC 30

( 2 ) INFORMATION FOR SEQ ID NO: 25:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: other nucleic acid ( i i i ) HYPOTHETICAL: NO ( x i ) SEQUENCE DESCRIPTION: SEQ ID NO: 25:

TTCTATTTTT GTACAAGACA GGGCTTG 27

( 2 ) INFORMATION FOR SEQ ID NO: 26:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: other nucleic acid ( i i i ) HYPOTHETICAL: NO (x i) SEQUENCE DESCRIPTION: SEQ ID NO: 26:

CAAGCCCTGT CTTGTACAAA AATAGAA 27

(2) INFORMATION FOR SEQ ID NO:27:

(i) SEQUENCE CHARACTERISTICS:
      (A) LENGTH: 114 amino acids
      (B) TYPE: amino acid
      (C) STRANDEDNESS: unknown
      (D) TOPOLOGY: unknown (ii) MOLECULE TYPE: protein (iii) HYPOTHETICAL: NO (xi) SEQUENCE DESCRIPTION: SEQ ID NO: 27:

```
Asp Val Leu Met Thr Gln Ile Pro Leu Ser Leu Pro Val Ser Leu
 1               5                  10                  15
Gly Asp Gln Ala Ser Ile Ser Cys Arg Ser Gln Asn Ile Val
                 20                  25                  30
His Ser Asn Gly Asn Thr Tyr Leu Asp Trp Tyr Leu Gln Lys Pro
                 35                  40                  45
Gly Gln Ser Pro Asn Leu Leu Ile Tyr Lys Val Ser Asn Arg Phe
                 50                  55                  60
Ser Gly Val Pro Asp Arg Phe Arg Gly Ser Gly Ser Gly Thr Asp
                 65                  70                  75
Phe Thr Leu Lys Ile Ser Arg Val Glu Ala Glu Asp Leu Gly Val
                 80                  85                  90
Tyr Tyr Cys Phe Gln Tyr Ser His Val Pro Trp Thr Phe Gly Gly
                 95                 100                 105
Gly Thr Lys Leu Glu Ile Lys Arg Ala
                110
```

(2) INFORMATION FOR SEQ ID NO: 28:

(i) SEQUENCE CHARACTERISTICS:
      (A) LENGTH: 123 amino acids
      (B) TYPE: amino acid
      (C) STRANDEDNESS: unknown
      (D) TOPOLOGY: unknown (ii) MOLECULE TYPE: protein (iii) HYPOTHETICAL: NO (xi) SEQUENCE DESCRIPTION: SEQ ID NO: 28:

```
Gln Val Gln Leu Gln Gln Pro Gly Ala Glu Leu Val Lys Pro Gly
 1               5                  10                  15
Ala Ser Val Lys Leu Ser Cys Lys Ala Ser Gly Tyr Thr Phe Thr
                 20                  25                  30
Asn Tyr Tyr Ile Tyr Trp Val Lys Gln Arg Pro Gly Gln Gly Leu
                 35                  40                  45
Glu Trp Ile Gly Gly Ile Asn Pro Thr Ser Gly Gly Ser Asn Phe
                 50                  55                  60
Asn Glu Lys Phe Lys Thr Lys Ala Thr Leu Thr Val Asp Glu Ser
                 65                  70                  75
Ser Thr Thr Ala Tyr Met Gln Leu Ser Ser Leu Thr Ser Glu Asp
                 80                  85                  90
Ser Ala Val Tyr Tyr Cys Thr Arg Gln Gly Leu Trp Phe Asp Ser
                 95                 100                 105
Asp Gly Arg Gly Phe Asp Phe Trp Gly Gln Gly Thr Thr Leu Thr
```

110                            115                            120

Val  Ser  Ser (2) INFORMATION FOR SEQ ID NO:29:

(i) SEQUENCE CHARACTERISTICS:
                (A) LENGTH: 16 amino acids
                (B) TYPE: amino acid
                (C) STRANDEDNESS: unknown
                (D) TOPOLOGY: unknown (ii) MOLECULE TYPE: protein (iii) HYPOTHETICAL: NO (xi) SEQUENCE DESCRIPTION: SEQ ID NO: 29:

Arg  Ser  Ser  Gln  Asn  Ile  Val  His  Ser  Asn  Gly  Asn  Thr  Tyr  Leu
        1                  5                               10                            15

Asp (2) INFORMATION FOR SEQ ID NO:30:

(i) SEQUENCE CHARACTERISTICS:
                (A) LENGTH: 7 amino acids
                (B) TYPE: amino acid
                (C) STRANDEDNESS: unknown
                (D) TOPOLOGY: unknown (ii) MOLECULE TYPE: protein (iii) HYPOTHETICAL: NO (xi) SEQUENCE DESCRIPTION: SEQ ID NO: 30:

Lys  Val  Ser  Asn  Arg  Phe  Ser
        1                  5

(2) INFORMATION FOR SEQ ID NO:31:

(i) SEQUENCE CHARACTERISTICS:
                (A) LENGTH: 9 amino acids
                (B) TYPE: amino acid
                (C) STRANDEDNESS: unknown
                (D) TOPOLOGY: unknown (ii) MOLECULE TYPE: protein (iii) HYPOTHETICAL: NO (xi) SEQUENCE DESCRIPTION: SEQ ID NO: 31:

Phe  Gln  Tyr  Ser  His  Val  Pro  Trp  Thr
        1                  5

(2) INFORMATION FOR SEQ ID NO:32:

(i) SEQUENCE CHARACTERISTICS:
                (A) LENGTH: 5 amino acids
                (B) TYPE: amino acid
                (C) STRANDEDNESS: unknown
                (D) TOPOLOGY: unknown (ii) MOLECULE TYPE: protein (iii) HYPOTHETICAL: NO (xi) SEQUENCE DESCRIPTION: SEQ ID NO: 32:

Asn  Tyr  Tyr  Ile  Tyr
        1                  5

(2) INFORMATION FOR SEQ ID NO:33:

(i) SEQUENCE CHARACTERISTICS:
    (A) LENGTH: 17 amino acids
    (B) TYPE: amino acid
    (C) STRANDEDNESS: unknown
    (D) TOPOLOGY: unknown (ii) MOLECULE TYPE: protein (iii) HYPOTHETICAL: NO (xi) SEQUENCE DESCRIPTION: SEQ ID NO: 33:

Gly Ile Asn Pro Thr Ser Gly Gly Ser Asn Phe Asn Glu Lys Phe
1               5                   10                  15

Lys Thr (2) INFORMATION FOR SEQ ID NO:34:

(i) SEQUENCE CHARACTERISTICS:
    (A) LENGTH: 14 amino acids
    (B) TYPE: amino acid
    (C) STRANDEDNESS: unknown
    (D) TOPOLOGY: unknown (ii) MOLECULE TYPE: protein (iii) HYPOTHETICAL: NO (xi) SEQUENCE DESCRIPTION: SEQ ID NO: 34:

Gln Gly Leu Trp Phe Asp Ser Asp Gly Arg Gly Phe Asp Phe
1               5                   10